United States Patent [19]

Tuong

[11] Patent Number: 5,395,950
[45] Date of Patent: Mar. 7, 1995

[54] PRODUCTION OF QUINIC ACID DERIVATIVES

[75] Inventor: Huynh-Ba Tuong, Pully, Switzerland

[73] Assignee: Nestec S.A., Vevey, Switzerland

[21] Appl. No.: 95,757

[22] Filed: Jul. 21, 1993

[30] Foreign Application Priority Data

Aug. 3, 1992 [EP]  European Pat. Off. ........... 92113189

[51] Int. Cl.⁶ .......................................... C07D 307/00
[52] U.S. Cl. .................... 549/302; 562/508; 549/362
[58] Field of Search ................. 549/302, 362; 562/508

[56] References Cited

U.S. PATENT DOCUMENTS

| | | | |
|---|---|---|---|
| 3,855,297 | 12/1974 | Diana et al. | 562/508 |
| 4,818,767 | 4/1989 | Rossignal | 562/508 |
| 4,940,803 | 7/1990 | Mills et al. | 549/302 |

FOREIGN PATENT DOCUMENTS 0802668 10/1958 United Kingdom.
8601508 3/1986 WIPO.

OTHER PUBLICATIONS

Ichikawa, et al., Chemical Abstracts, vol. 116, No. 23, No. 236095z (1992).
Wynne et al CA 106(9) 64477a 1986.
Haslam, et al., "Synthesis and Properties of Some Hydboxycinnamoyl Esters of Quinic Acid," J. Chem. Soc. pp. 2137–2146 (1964).

Primary Examiner—C. Warren Ivy
Assistant Examiner—A. A. Owens
Attorney, Agent, or Firm—Vogt & O'Donnell

[57] ABSTRACT

1-, 5-O-mono- and 3,4-0-bis-substituted derivatives of quinic acid are prepared by reacting a derivative of a hydroxycinnamic acid of which the hydroxyl group(s) is/are protected with a quinic acid derivative to form an ester and the protective groups are then cleaved under controlled conditions of acidity and temperature. These conditions provide for regiospecificity of the esterification and enable any degradation of isomerization to be avoided. The process gives new quinides in high yields.

7 Claims, No Drawings

PRODUCTION OF QUINIC ACID DERIVATIVES

BACKGROUND OF THE INVENTION

This invention relates to new derivatives of quinic acid and to a process for their production.

Derivatives of quinic acid are widespread in the vegetable world. The chlorogenic acid content of green coffee beans, for example, can represent up to 10% of the dry matter. The term "chlorogenic acid" in fact encompasses a relatively complex mixture of quinic acid derivatives, including caffeoyl, dicaffeoyl, p-coumaroyl, feruloyl and caffeoylferuloyl quinic acids. After roasting, the coffee grains contain an even more complex mixture of compounds of which some are formed by lactones of quinic acids known as quinides or even other isomers formed during the heat treatment. Some of these derivatives show antimicrobial activity, opiate antagonistic activity, anti-inflammatory activity, fungistatic activity, cytostatic activity and inhibiting activity in the biosynthesis of leucotrienes. Applicants have found that some of these compounds show antiurease activity, their use being the subject of a copending application filed by applicants under the title "An Anti-Urease Cosmetic or Dermatological Composition".

The synthesis of hydroxycinnamoyl quinic acids is described, for example, by E. Haslam et al. in J. Chem. Soc. 1964, 2137-2146. However, the known processes involve a delicate and laborious separation step based on the technique of countercurrent distribution in order to isolate the required compound in cases where the key esterification step is not regioselective and leads to an isomer mixture which has to be separated. In addition, the known method uses protective groups for the hydroxycinnamic reactants which can only be cleaved under drastic conditions (strong acid or strong base and heat), resulting in isomerization of the chlorogenic derivatives.

SUMMARY OF THE INVENTION

The invention relates to new derivatives of quinic acid, i.e. quinides corresponding to the general formula:

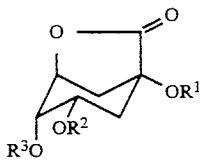

in which $R^1$ is H and $R^2$ and $R^3$ may be the same or different and represent a group corresponding to the formula:

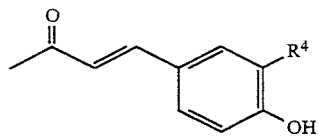

and $R^4$ is H, $OCH_3$ or OH or $R^1$ is a group corresponding to the formula:

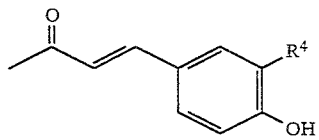

in which $R^4$ is as defined above and $R^2$ and $R^3$ represent H.

The new compounds according to the invention are very useful intermediate products for the production of quinic acids having the interesting applications mentioned above.

In addition, 3,4-O-dicaffeoyl quinide has shown a negative inotropic effect. 3,4-O-diferuloyl quinide has also shown in vitro inhibition of platelet aggregation induced by arachidonic acid in a dose of 5 microg/ml.

The present invention also relates to a process for the production of 1- or 5-monosubstituted or 3,4-bis-substituted derivatives of quinic acid, in which a derivative of a hydroxycinnamic acid, of which the hydroxyl group(s) is/are protected, is reacted with a derivative of quinic acid to form an ester, after which the protective group(s) is/are cleaved. This process is characterized in that, in the case of the 1-monosubstituted and 3,4-bis-substituted derivatives, the quinic acid derivative used is a quinide and in that the final quinic acid derivative is obtained by acidic hydrolysis of the quinide under controlled conditions and in that the protective group(s) is/are cleavable under controlled conditions of acidity and temperature, these controlled conditions providing for regiospecificity of the esterification and enabling any degradation or isomerization to be avoided.

DETAILED DESCRIPTION OF THE INVENTION

In a first embodiment of the process according to the invention, 1-O-hydroxycinnamoyl derivatives of quinide are prepared in a high yield and are then converted into quinic acid. To this end, the OH functions in the 3, 4 and 5 positions and the carboxyl function in the 1 position of the quinic acid are protected, for example by reaction with acetone in the presence of p-toluene sulfonic acid, which leads to 3,4-O-isopropylidene quinide. Accordingly, only the hydroxyl group in the 1 position is available for esterification by a reactive derivative of a hydroxycinnamic acid of which the phenol function(s) has/have been protected. The reactive derivative in question may be, for example, an anhydride or preferably an acid chloride.

The group selected to protect the phenol function is a carbonate, for example trichloroethyl carbonate in the case of p-coumaric acid and ferulic acid, which may be cleaved under moderate conditions, for example with zinc in acetic medium at ambient temperature. In the case of caffeic acid, it is preferred to use methyl carbonate which may readily be cleaved under moderate conditions, for example with lithium chloride in the presence of trichloromethyl silane in boiling pyridine without any detectable isomerization occurring.

Before cleavage of the carbonate protecting the hydroxycinnamic acid, the acetonide group protecting the OH functions in the 3 and 4 positions of the quinide has to be released. A highly concentrated aqueous solution of trifluoroacetic acid at ambient temperature is used for this purpose which makes it possible to avoid the decomposition that would occur under the conventional conditions where acetic acid is used at high temperatures. Finally, to produce the quinic acids corresponding to the quinides, the quinides are subjected to acidic hydrolysis, again under controlled conditions, for example with concentrated hydrochloric acid in a polar solvent, for example tetrahydrofuran, at low temperatures, preferably of the order of 0° C.

In a second embodiment of the process according to the invention for the production of 3,4-bis-substituted derivatives, the starting product used is the above 3,4-O-isopropylidene quinide of which the 1 position is protected. The protective group used is preferably trichloroethyl carbonate. The OH functions in the 3 and 4 positions are then made accessible by cleavage of the protective acetonide group, as described above. The unprotected quinide is then reacted with a derivative of hydroxycinnamic acid of which the phenol function(s) has/have been protected. This reactive derivative may be, for example, an anhydride or preferably an acid chloride. As mentioned above in connection with the first embodiment, trichloroethyl carbonate protective groups are preferably used to produce the p-coumaroyl and feruloyl derivatives while methyl carbonate is used for the caffeoyl derivatives. The protective groups are then cleaved and the lactone ring of the quinide is opened as described above.

In a third embodiment of the process according to the invention intended for the production of substituted 5-hydroxycinnamoyl quinic acids, the starting material is a 3,4-O-quinide protected, for example, by an acetonide group of which the lactone ring is then opened to release the OH function in the 5 position to enable it to be esterified after the carboxyl group has been protected. A phenacyl halide, for example phenacyl bromide, is used for this purpose, enabling the carboxyl function in the 1 position to be esterified and hence protected by a labile group after the lactone ring has been opened with sodium bicarbonate. The phenacyl ester used may be cleaved under controlled conditions, for example with zinc in acetic acid at ambient temperature. The OH function in the 5 position is then esterified with a reactive derivative of a hydroxycinnamic acid of which the phenol function(s) has/have been protected, for example by trichloroethyl carbonate in the case of the p-coumaric and ferulic acids and by methyl carbonate or benzylidene in the case of caffeic acid. After the esterification, the various protective groups are sequentially cleaved, beginning with the release of the groups of the peripheral substituents, for example the phenacyl groups protecting the carboxyl function in the 1 position and carbonate and then, optionally, the benzylidene group protecting the phenol functions of the hydroxycinnamic acids and the acetonide group protecting the OH functions in the 3 and 4 positions of the quinic acid skeleton. The benzylidene group may readily be cleaved with trifluoroacetic acid in the presence of water at ambient temperature. The other protective groups may also be cleaved under the moderate conditions mentioned above.

The compounds prepared in these various embodiments are obtained in very high yields because each step is completed without isomerization and the compounds may then readily be purified.

EXAMPLES

The invention is illustrated by the following Examples in which parts and percentages are by weight, unless otherwise indicated.

The starting compounds and the reactants all come from Fluka AG. The solvents were made anhydrous before use. The medium pressure liquid chromatography (MPLC) was carried out using Büchi chromatograph. The polyamide used for the chromatography was previously washed with methanol and then dried before use. The structure of the compounds was verified by nuclear magnetic resonance of the proton (NMR). The results of the elemental analyses, the yields and the melting points are shown.

Examples 1-3

1. Synthesis of 1-O-p-coumaroyl quinide and 1-O-p-coumaroyl quinic acid 1.1. 3,4-O-isopropylidene quinide A suspension of 66.2 g (344.4 mmol) and 2.1 g (11 mmol) p-toluene sulfonic acid in 900 ml acetone is refluxed for 24 h in a Soxhlet extractor containing 90 g 4 A° molecular sieve. After cooling to 0° C., 27 g (321.4 mmol) sodium bicarbonate are added. After the reaction mixture has been stirred for 1 h at the temperature of 0° C., the suspension is filtered and the solvent is evaporated. Recrystallization of the residue from a mixture of dichloromethane and hexane gives 67 g 3,4-O-isopropylidene quinide, Mp. 141°-142° C,, in a yield of 91%.

1.2. 1-O-carbotrichloroethoxy-p-coumaroyl-3,4-O-isopropylidene quinide 5.7 g (16 mmol) carbotrichloroethoxy-p-coumaric acid chloride are added at 0° C. to a solution of 3.2 g (15mmol) 3,4-O-isopropylidene quinide and 1.42 g (18 mmol) pyridine in 80 ml dichloromethane. After stirring for 24 h at ambient temperature, the solvents are removed by evaporation. The residue is taken up in ethyl acetate, rinsed with a 0.5N aqueous solution of HCl and then with brine, the solution is dried over sodium sulfate and the solvent is evaporated. Recrystallization of the residue from ethanol gives 6.58 g 1-O-carbotrichloroethoxy-p-coumaroyl--3,4-O-isopropylidene quinide (Mp. 178°-182° C., yield 82%).

1.3. 1-O-carbotrichloroethoxy-p-coumaroyl quinide

A solution of 5.36 g (10 mmol)1-O-carbotrichloroethoxy-p-coumaroyl-3,4-O-isopropylidene quinide in 22 ml of a 90% aqueous solution of trifluoroacetic acid is stirred for 2 h at ambient temperature. Evaporation of the solvents in a water jet pump vacuum and trituration of the residue in 30 ml ether gives 3.71 g 1-O-carbotrichloroethoxy-p-coumaroyl quinide (Mp. 221°-224° C., yield 75%).

1.4. 1-O-p-coumaroyl quinide 1.9 g (30 mmol) zinc powder is added to a solution of 2.76 g (5.7 mmol) 1-O-carbotrichloroethoxy-p-coumaroyl quinide in 30 ml dioxane. After stirring for 3 h at ambient temperature, the solvents are removed by evaporation. The residue is then taken up in 50 ml ethyl acetate, the solution is rinsed with a 0.5N aqueous solution of HCl and then with brine, decanted and the organic phase is dried over sodium sulfate. Evaporation of the solvent and recrystallization of the residue from acetonitrile gives 1.39 g 1-O-p-coumaroyl quinide (Mp. 212°-216° C., yield 78%). Elemental analysis: calculated C 60.00, H 5.04; found C 59.87, H 5.12.

1.5. 1-O-p-coumaroyl quinic acid 15 ml 5N HCl are added to a solution of 2.8 g (8.74 mmol) 1-O-p-coumaroyl quinide in 15 ml tetrahydrofuran (THF) at 0° C. After stirring for 24 h at ambient temperature, the reaction mixture is diluted with 20 ml THF, after which solid sodium bicarbonate is added in portions with stirring at pH 3. After saturation of the solution with NaCl, the aqueous phase is collected and extracted with 3×30 THF. The combined organic phases are then dried and the solvent is evaporated. Precipitation of the residue with a mixture of chloroform and THF followed by freeze drying gives 2.09 g 1-O-p-coumaroyl quinic acid (yield 71%). Elemental analysis: calculated C 56.80, H 5.36; found C 56.54, H 5.54.

2. Synthesis of 1-O-feruloyl quinide and 1-O-feruloyl quinic acid

Following procedure described in paragraphs 1.2 to 1.5 above, the following compounds are successively obtained:

2.1. 1-O-carbotrichloroethoxyferuloyl-3,4-O-isopropylidene quinide (Mp. 159°–161.5° C., yield 76%).

2.2. 1-O-carbotrichloroethoxyferuloyl quinide (Mp. 176°–178.5° C., yield 73%).

2.3. 1-O-feruloyl quinide (Mp. 205°–207.5° C., yield 85%), elemental analysis: calculated C 58.29, H 5.18; found C 58.08, H 5.37.

2.4. 1-O-feruloyl quinic acid (yield 72%), elemental analysis: calculated C 55.43, H 5.47; found C 55.12, H 5.35.

3. Synthesis of 1-O-caffeoyl quinide and 1-O-caffeoyl quinic acid

Following the procedure described in paragraphs 1.2 to 1.3 and 1.5 above, but using methyl carbonate as the protective group for the phenol functions of the caffeic acid, the following compounds are successively obtained:

3.1. 1-O-dicarbomethoxycaffeoyl-3,4-O-isopropylidene quinide, the quinide being purified by chromatography of the residue in a polyamide column using a mixture of 1 volume dichloromethane to 3 volumes hexane as eluent (yield 57%).

3.2. 1-O-dicarbomethoxycaffeoyl quinide (yield 62%).

3.3. 1-O-caffeoyl quinide (Mp. 225°–229° C. with decomposition, yield 75%), elemental analysis: calculated C 57.14, H 4.80; found C 57.11, H 4.91.

3.4. 1-O-caffeoyl quinic acid (yield 72%), elemental analysis: calculated C 54.24, H 5.12; found C 53.97, H 5.21.

In step 3.3, cleavage of the protective groups differs from the preceding step 1.4 and is carried out as follows: a solution of 5.5 g (12.16 mmol) 1-O-dicarbomethoxycaffeoyl quinide and 5.43 g (50 mmol) chlorotrimethyl silane in 50 ml pyridine is refluxed for 1 hour. 5.3 g (122 mmol) LiCl are then added and refluxing is continued for 1 hour. After removal of the pyridine by evaporation, the residue is taken up in 100 ml ethyl acetate, rinsed with an aqueous solution of 1N HCl and then with brine and the organic phase is dried over sodium sulfate. After reduction of the volume of the solution to 30 ml, 70 ml hexane are added and, finally, the solid residue is recrystallized from ethyl acetate.

Examples 4–5

4. Synthesis of 5-O-feruloyl quinic acid 4.1. Phenacyl-3,4-O-isopropylidene quinic A suspension of 1.07 g (5 mmol) 3,4-O-isopropylidene quinide in 5 ml of a 1M aqueous solution of sodium bicarbonate is refluxed for 1 h. After removal of the water in vacuo, the residue is triturated in a mixture of equal volumes of ethanol and toluene and then concentrated to dryness. Trituration and drying are repeated 3 times. The white solid obtained is treated with 1 g (5 mmol) phenacyl bromide in 10 ml dimethyl formamide for 1 h. After evaporation of the solvent in vacuo, the residue is dissolved in 20 ml dichloromethane, washed with water and dried over sodium sulfate and the solvent is evaporated. Recrystallization of the residue from ethyl acetate gives 1.46 g phenacyl-3,4-O-isopropylene quinate (Mp. 136°–139° C., yield 84%).

4.2. Phenacyl-5-O-carbotrichloroethoxyferuloyl-3,4-O-isopropylidene quinate

A solution of 3.5 g (10 mmol) phenacyl-3,4-O isopropylidene quinate and 0.87 g (11 mmol) pyridine in 30 ml dichloromethane is added at −10° C. to a solution of 3.88 g (10 mmol) carbotrichloroethoxyferulic acid chloride in 10 ml dichloromethane. After stirring for 24 h at ambient temperature, the reaction mixture is washed with a 0.5N aqueous solution of HCl decanted, the organic phase is dried over sodium sulfate and the solvent is evaporated. The residue is chromatographed in a column of silica gel eluted with dichloromethane, after which the product is treated with a mixture of 1 volume benzene to 4 volumes hexane which gives an amorphous residue of 2.84 g of phenacyl-5-O-carbotrichloroethoxyferuloyl-3,4-O-isopropylidene quinate (yield 41%).

4.3. 5-O-feruloyl-3,4-O-isopropylidene quinic acid

A solution of 0.2 g (0.29 mmol) 5-O-carbotrichloroethoxyferuloyl-3,4-O-isopropylidene quinate in 2 ml glacial acetic acid is treated with 0.5 g (7.65 mmol) zinc powder for 30 minutes, after which 15 mol hexane are added. After removal of the solvents by filtration, 10 ml dichloromethane are added to the residue which is then treated at 0° C. with an aqueous solution of 1N HCl, the organic phase is separated and the aqueous phase is then extracted with 3×10 ml dichloromethane. The combined organic phases are then washed with brine and dried over sodium sulfate and the solvent is eliminated by evaporation. The residue is taken up in a mixture of equal volumes of dichloromethane and hexane, giving 0.07 g 5-O-feruloyl-3,4-O-isopropylidene quinic acid (yield 62%).

4.4. 5-O-feruloyl quinic acid

A solution of 0.06 g (0.15 mmol) 5-O-feruloyl-3,4-O-isopropylidene quinic acid in 4 ml of a 90% aqueous solution of trifluoroacetic acid is stirred for 30 minutes. Removal of the solvents in vacuo and treatment of the residue with a mixture of 1 volume ethyl acetate and 4 volumes hexane gives 0.03 g 5-O-feruloyl quinic acid (yield 54%).

5. Synthesis of 5-O-caffeoyl quinic acid 5.1. 3,4-benzylidenedioxy benzaldehyde

A mixture of 13.8 g (100 mmol) 3,4-dihydroxybenzaldehyde, 19.3 g (120 mmol) benzylidene chloride and 16.6 g (120 mmol) potassium carbonate in 50 ml dimethyl formamide is heated with stirring for 24 h to 100° C. After evaporation of the solvent in vacuo, 200 ml ether are added to the residue which is then washed with brine and dried over sodium sulfate, after which the ether is evaporated. Recrystallization of the residue from hexane gives 13.5 g 3,4-benzylidenedioxy benzaldehyde (Mp. 82°–84° C., yield 60%).

5.2. 3,4-O-benzylidene caffeic acid

A solution of 3.4 g (15 mmol) 3,4-benzylidene dioxybenzaldehyde and 1.19 g (11.43 mmol) malonic acid in 15 ml pyridine and 0.5 ml piperidine is refluxed for 1 h. After evaporation of the solvents, the residue is treated with 8 ml concentrated HCl in 50 g ice and is then extracted with 3×50 ml of a mixture of 9 volumes ethyl acetate to 1 volume THF. The combined extracts are then washed with brine and dried over sodium sulfate, after which the solvent is removed by evaporation. Washing of the residue with toluene followed by recrystallization from ethyl acetate gives 2.53 g 3,4-O-benzylidene caffeic acid (Mp. 185°–188° C., yield 82%).

5.3. Phenacyl-5-O-benzylidene caffeoyl-3,4-O-isopropylidene quinate 0.72 g (3.6 mmol) dicyclohexyl carbodiimide is added at 0° C. to a suspension of 1.05 g (3 mmol) phenacyl-3,4-O-isopropylidene quinate, 0.8 g (3 mmol) 3,4-O-benzylidene caffeic acid and 0.44 g (0.3 mmol) 4-pyrrolidinopyridine in 14 ml dichloromethane and the mixture is left to react at ambient temperature for 4 h. The reaction mixture is then successively washed with 2×5 ml of a 0.1N aqueous solution of HCl and 2×5 ml brine and dried over sodium sulfate, after which the solvents are removed by evaporation. The residue is chromatographed in a column of silica gel using dichloromethane as eluent and phenacyl-5-O-benzylidene caffeoyl-3,4-O-isopropylidene quinate is collected in a quantity of 0.8 g (yield 45%).

5.4. 5-O-benzylidene caffeoyl-3,4-O-isopropylidene quinic acid

5-O-benzylidene caffeoyl-3,4-O-isopropylidene quinic acid (yield 88%) is obtained in the same way as described in paragraph 4.3 above except that the residue of the first step is treated with ethyl acetate instead of dichloromethane and with an aqueous solution of 2N HCl instead of a solution having a concentration of 1N.

5.5. 5-O-caffeoyl quinic acid

5-O-caffeoyl quinic acid (yield 86%) is obtained in the same way as described in paragraph 4.4 above, except that the product is recrystallized from water, elemental analysis: calculated C 54.24, H 5.12; found C 54.03, H 4.97.

Examples 6-8

6. Synthesis of 3,4-O-di-p-coumaroyl quinide and 3,4-O-di-p-coumaroyl quinic acid 6.1. 1-O-carbotrichloroethoxy-3,4-O-isopropylidene quinide 34.96 g (165 mmol) trichloroethyl chloroformate diluted in 30 ml dichloromethane is added dropwise at 0° C. to a solution of 32.1 g (150 mmol) 3,4-O-isopropylidene quinide and 28.9 g (365 mmol) pyridine in 300 ml dichloromethane. After stirring for 3 hours at ambient temperature, the reaction mixture is washed with an aqueous solution of 2 N HCl and then with water, the solution is dried over sodium sulfate and the solvents are evaporated. Recrystallization of the residue from ethanol gives 49.5 g 1-O-carbotrichloroethoxy-3,4-O-isopropylidene quinide (Mp. 165°–166° C., yield 85%).

6.2. 1-O-carbotrichloroethoxy quinide

A solution of 39 g (100 mmol) 1-O-carbotrichloroethoxy-3,4-O-isopropylidene quinide in 60 ml of a 90% aqueous solution of trifluoroacetic acid is stirred for 3 h. After removal of the solvents, the residue is dissolved in 100 ml ethyl acetate and washed with a 2% aqueous solution of sodium bicarbonate and then with brine, dried over sodium sulfate and the solvent is evaporated. Recrystallization of the residue from toluene gives 24.6 g 1-O-carbotrichloroethoxy quinide (Mp. 130°–131° C., yield 70%).

6.3. 3,4-O-bis-carbotrichloroethoxy-p-coumaroyl-1-O-carbotrichloroethoxy quinide 7.88 g (22 mmol) carbotrichloroethoxy-p-coumaric acid chloride are added to a solution of 3.5 g (10 mmol) 1-O-carbotrichloroethoxy quinide and 1,74 g (22 mmol) pyridine in 100 ml dichloromethane. After stirring for 24 h, the reaction mixture is washed with a 0.5N aqueous solution of HCl and then with water and dried over sodium sulfate and the solvents are removed by evaporation. Recrystallization of the residue from a mixture of ethyl acetate and hexane gives 5.3 g 3,4-O-bis-carbotrichloroethoxy-p-coumaroyl-1-O-carbotrichloroethoxy quinide (Mp. 214°–218° C., yield 54%).

6.4. 3,4-O-di-p-coumaroyl quinide 13.4 g (13.5 mmol) 3,4-O-bis-carbotrichloroethoxy-p-coumaroyl-1-O-carbotrichloroethoxy quinide in 200 ml THF and 75 ml acetic acid are treated with 14 g (215 mmol) zinc powder for 90 mins. at ambient temperature. After removal of the residue, the solvent is evaporated from the filtrate. 200 ml ethyl acetate are then added to the residue, the solution is washed with an aqueous solution of 0.5N HCl and then with brine, dried over sodium sulfate and the solvent is evaporated. Recrystallization of the crude product from ethyl acetate gives 4.33 g 3,4-O-di-p-coumaroyl quinide (Mp. 233°–235° C., yield 69%), elemental analysis: calculated C 64.38, H 4.75; found C 64.58, H 4.98.

6.5 3,4-O-di-p-coumaroyl quinic acid

A solution of 2.8 g (6 mmol) 3,4-O-di-p-coumaroyl quinide and 0.1 ml trifluoroacetic acid in 60 ml 80% aqueous THF is refluxed for 3 days. After removal of the solvents, 30 ml ethyl acetate are added to the residue, the solution is washed with brine and dried over sodium sulfate and the solvent is evaporated. Recrystallization of the residue from a mixture of 1 volume ethyl acetate to 5 volumes dichloromethane gives 1.94 g 3,4-O-di-p-coumaroyl quinic acid (yield 67%), elemental analysis: calculated C 61.98, H 4.99; found C 61.90, H 5.11.

7. Synthesis of 3,4-diferuloyl quinide and 3,4-O-diferuloyl quinic acid

Following procedure described in paragraphs 6.3 to 6.5 above, the following compounds are successively obtained:

7.1. 3,4-O-bis-carbotrichloroethoxyferuloyl-1-O-carbotrichloroethoxy quinide (Mp. 234°–235° C., yield 67%); final residue recrystallized from a mixture of chloroform and hexane.

7.2. 3,4-O-diferuloyl quinide (yield 77%), elemental analysis: calculated C 61.60, H 4.98; found C 61.82, H 5.24; crude product recrystallized from toluene.

7.3. 3,4-O-diferuloyl quinic acid (yield 65%), elemental analysis: calculated C 59.56, H 5.18; found C 59.30, H 5.16.

8 Synthesis of 3,4-O-dicaffeoyl quinide and 3,4-O-dicaffeoyl quinic acid 8.1 3,4-O-bis-dicarbomethoxycaffeoyl-1-O-carbotrichloroethoxy quinide 31.4 g (100 mmol) dicarbomethoxycaffeic acid chloride are added at 0° C. to a solution of 17.9 g (50 mmol) 1-O-carbotrichloroethoxy quinide and 7.9 g (100 mmol) pyridine in 150 ml dichloromethane. After stirring for 2 days at −10° C., the reaction mixture is washed with an aqueous solution of 1N HCl and then with water and dried over sodium sulfate, after which the solvents are evaporated. MPLC of the residue in a polyamide column using a mixture of 1 volume dichloromethane to 4 volumes hexane as eluent gives 23.7 g 3,4-O-bis-dicarbomethoxycaffeoyl-1-O-carbotrichloroethoxy quinide (yield 52%).

8.2. 3,4-O-dicaffeoyl quinide 5.8 g (6.4 mmol) 3,4-O-bis-dicarbomethoxycaffeoyl-1-O-carbotrichloroethoxy quinide and 2.8 g (64mmol) LiCl are refluxed for 2 h in 60 ml pyridine. After removal of the solvent, 200 ml ethyl acetate are added to the residue, the solution is washed with a 1N aqueous solution of HCl and then with brine and dried over sodium sulfate, after which the solvent is evaporated. MPLC of the residue in a column of polyamide using a mixture of 6 volumes ethyl acetate to 1 volume methanol as eluent, followed by freeze drying, gives 2.38 g 3,4-O-dicaffeoyl quinide (yield 75%), elemental analysis: calculated C 60.24, H 4.45; found C 60.07, H 4.62.

8.3 3,4-O-dicaffeoyl quinic acid

A solution of 2 g (4 mmol) 3,4-O-dicaffeoyl quinide and 20 drops trifluoroacetic acid in 20 ml 50% aqueous acetonitrile is refluxed for 24 h. After evaporation of the solvents, the residue is dissolved in 200 ml water and washed with 3×20 ml ether. After decantation, the aqueous phase is collected and freeze-dried, which gives 1.25 g 3,4-O-dicaffeoyl quinic acid (yield 61%), elemental analysis: calculated C 58.14, H 4.68; found C 58.34, H 4.92.

I claim:

1. A process for the production of 1- or 5-monosubstituted or 3,4-bis-substituted derivatives of quinic acid, in which a derivative of a hydroxycinnamic acid, of which the hydroxyl group(s) is/are protected, is reacted with a derivative of quinic acid to form an ester, after which the protective group(s) is/are cleaved, characterized in that, in the case of the 1-monosubstituted and 3,4-bis-substituted derivatives, the quinic acid derivative used is a quinide and in that the final quinic acid derivative is obtained by acidic hydrolysis of the quinide under controlled conditions and in that the protective group(s) is/are cleavable under controlled conditions of acidity and temperature, these controlled conditions providing for regiospecificity of the esterification and enabling any degradation or isomerization to be avoided.

2. A process as claimed in claim 1 for the production of 1-O-hydroxycinnamoyl derivatives, characterized in that the OH functions in the 3 and 4 positions of the quinide are protected by reaction with acetone which leads to 3,4-O-isopropylidene quinine and the hydroxyl group in the 1 position is esterified with a reactive derivative of a hydroxycinnamic acid of which the phenol function(s) has/have been protected.

3. A process as claimed in claim 2 for the production of 1-O-p-coumaroyl or 1-O-feruoyl derivatives, characterized in the protective group of the phenol function is trichloroethyl carbonate, the acetonide group protecting the 3 and 4 positions is released with aqueous trifluoroacetic acid at ambient temperature and the trichloroethyl carbonate is then cleaved with zinc in acetic medium at ambient temperature.

4. A process as claimed in claim 2 for the production of 1-O-p-caffeoyl derivatives, characterized in that the protective group of the phenol functions is methyl carbonate, the acetonide group protecting the 3 and 4 positions is released with aqueous trifluoroacetic acid at ambient temperature and the methyl carbonate is cleaved with lithium chloride in the presence of trichloromethyl silane in pyridine.

5. A process as claimed in claim 1 for the production of 3,4-bis-substituted derivatives, characterized in that quinic acid is reacted with acetone, the 1 position of the 3,4-isopropylidene quinide is protected with trichloroethyl carbonate, the acetonide group protecting the 3 and 4 positions is cleaved, the unprotected quinide is reacted with a derivative of hydroxycinnamic acid of which the phenol function(s) is/are protected by a carbonate group and the protective carbonate groups are cleaved.

6. A process as claimed in claim 1 for the production of a 5-O-hydroxycinnamoyl quinic acid, characterized in that quinide is reacted with acetone, the lactone ring of the 3,4-isopropylidene quinide is opened with sodium bicarbonate, the compound obtained is reacted with a phenacyl halide to protect the carboxyl group released in the 1 position by a phenyl ester group, the OH function in the 5 position is esterified with a reactive derivative of a hydroxycinnamic acid of which the phenol function(s) is/are protected with trichloroethyl carbonate in the case of p-coumaric and ferulic acids and by methyl carbonate or benzylidene in the case of caffeic acid and the protective phenacyl, carbonate and optionally benzylidene groups are successively cleaved.

7. A process as claimed in any of claims 1 to 5, characterized in that the quinide is converted into quinic acid by controlled acidic hydrolysis with concentrated hydrochloric acid at low temperatures in the presence of a polar solvent.

* * * * *

UNITED STATES PATENT AND TRADEMARK OFFICE
CERTIFICATE OF CORRECTION

PATENT NO. : 5,395,950
DATED      : March 7, 1995
INVENTOR(S): Tuong HUYNH-BA

It is certified that error appears in the above-indentified patent and that said Letters Patent is hereby corrected as shown below:

On the title page, item [19] "Tuong" should read --Huynh-Ba--.
Item [75]: Inventor should rad --Tuong Huynh-Ba--.

Signed and Sealed this

Thirtieth Day of May, 1995

*Attest:*

BRUCE LEHMAN

*Attesting Officer*        *Commissioner of Patents and Trademarks*